June 25, 1974 TAKEO YUGE Plant Pat. 3,577
AZALEA PLANT
Filed Jan. 15, 1973
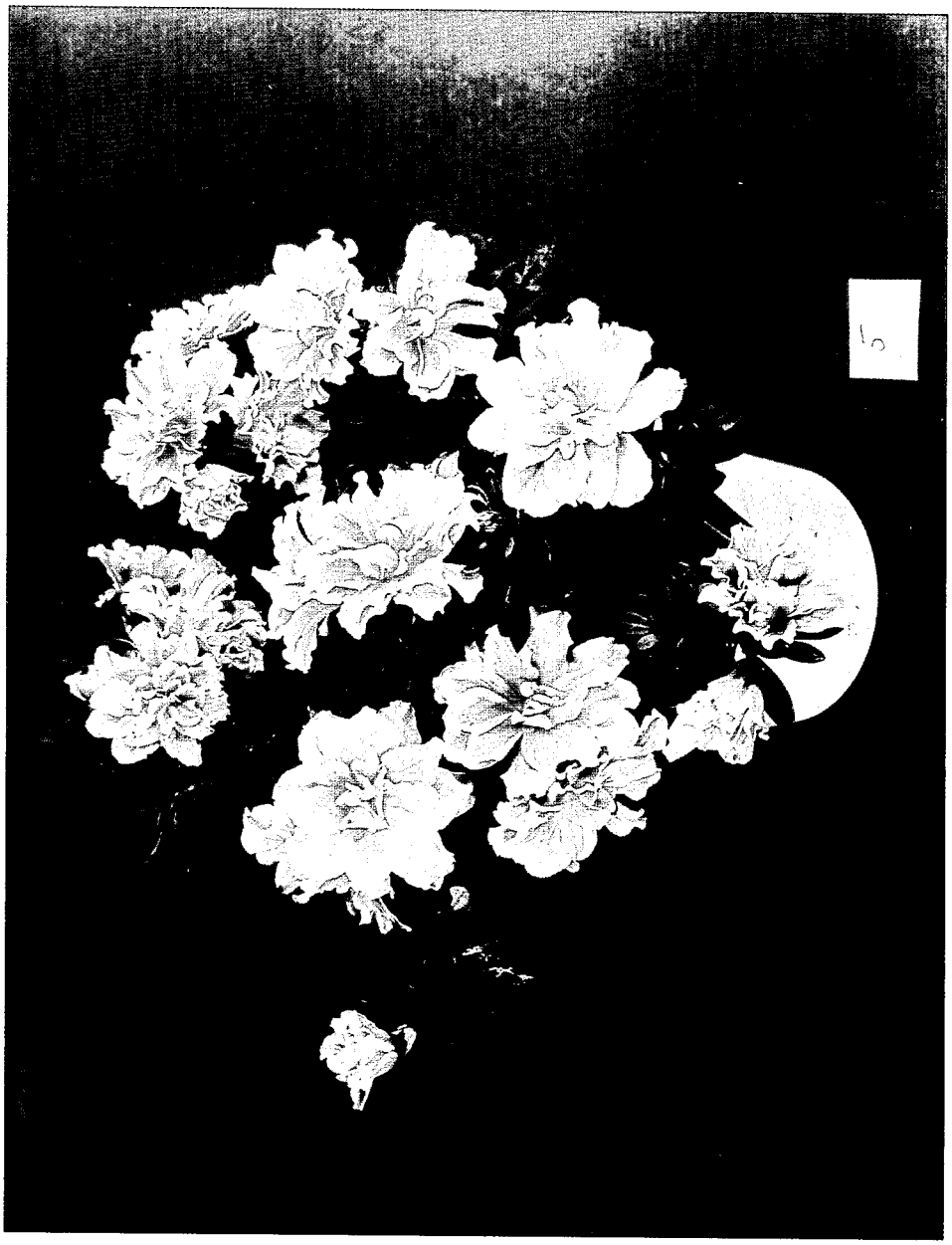

United States Patent Office

Plant Pat. 3,577
Patented June 25, 1974

3,577
AZALEA PLANT

Takeo Yuge, Altadena, Calif., assignor to Geo. J. Ball, Inc., West Chicago, Ill.

Filed Jan. 15, 1973, Ser. No. 323,916
Int. Cl. A01h 5/00
U.S. Cl. Plt.—55 1 Claim

ABSTRACT OF THE DISCLOSURE

A new variety of azalea plant adapted for pot-forcing and characterized by its profuse and early spring production of large red and white variegated flowers, the red coloring of the petals extending outwardly from the petal base and being incised into a pure white petal margin.

BACKGROUND OF THE INVENTION

This new variety of azalea originated as a seedling of Bonanza × Avenir developed by me in connection with my breeding program being carried on at Altadena, Calif., with the object of developing new and commercially valuable varieties of azalea plants. This variety was selected by me for propagation and test because of the very attractive coloring and abundant production of its relatively large blossoms and subsequent asexual propagation of the new plant, under my direction and by cuttings at San Fernando, Calif., has demonstrated the plant to be a good grower with permanently fixed characteristics of flower size and coloring. Commercial propagation of the new plant by means of cuttings is now being carried on at Salem, Oreg., and at San Fernando, Calif.

DESCRIPTION OF THE DRAWING

My new variety of azalea plant is illustrated by the accompanying photographic drawing in full color which shows a potted plant in full bloom, the color shown being as nearly true as can be had by conventional photographic procedures.

DESCRIPTION OF THE NEW PLANT

The following is a detailed description of my new azalea variety, with the color designations according to the Horticultural Colour Chart produced by Robert F. Wilson, and issued by the British Colour Council, in collaboration with The Royal Horticultural Society.

*The plant*

Origin: Seedling.
Parentage: Seed parent—Bonanza (unpatented). Pollen parent—Avenir (unpatented).
Classification: Azalea hybrid.
Form: Bush, as a potted plant.
Growth: Vigorous, upright and with sturdy, limber and spreading branches.
Foliage: Moderate in quantity.
Leaf Shape.—Obovate. Size: Variable, up to 2 inches long when mature. Texture: Leathery and hirsute. Color: Upper side—Ivy Green 0001060/1; under side—Spinach Green 0960/3. Petioles: ¼ inch long. Ribs and veins: Netted.

*The bud*

Form: Urn shaped.
Size: Fairly small. Diameter—½ to ⅝ inch. Depth—¾ to ⅞ inch.
Opening: Bud opens slowly.

Color: When sepals first divide—Pod Green 061. When peals begin to unfurl—Neyron Rose 623/2, broadly marginal with white.
Sepals: Upstanding and pointed.
Calyx: Small and funnel-shaped. Calyx splits and has a hairy aspect.
Peduncle: Erect, short and hairy.
*Color.*—Fern Green 0862, sometimes overlaid with Delft Rose 020/0.

*The flower*

Blooming habit: Intermitten. Blooming once in early spring with profuse production of blossoms.
Size: Large—2¾ to 3 inches in diameter and ⅝ inch in depth.
Borne: In clusters.
Shape: Urceolate at beginning, becoming funnel-shaped as blossom matures.
Petalage: Petals average 23 to 25 in number.
*Form.*—Ovate with obtuse apex. Marginally undulate.
*Arrangement.*—Double.
*Color.*—Outer petals—Base and main body are slightly darker than Rose Madder 23/3 with the color incised into broad white margins, the petals comprising standard are blotched with Tyrian Rose 24/1 lightly overlaid with Oxblood Red 00823/3. Inside petals—Color is similar to that of outer petals except the blotching and shading is Spiraea Red 025. Reverse side—White margin becoming incised with Tyrian Rose 24/2 which main body of petal, except for base, is Rhodonite Red 0022.
*Texture.*—Soft.
*Discoloration.*—Very slight.
Petaloids: Variable in number and of small size.
*Color.*—Similar to that of the inside petals.
Peduncle: ¼ to ½ inch long, sturdy and upright.
*Color.*—Basal color is Fern Green 0862, sometimes overlaid with Delft Rose 0201.
Persistence: Petals hang on and dry.
Fragrance: Very faint.
Disease resistance: This plant resists all known diseases prevalent in the areas where this plant is grown.
Lasting quality: On plant—good. Not used for cut flowers.

*Reproductive organs*

Stamens: Anthers and filaments—none observed.
*Pollen.*—None observed.
Pistils: 1 in number, 1 to 1¼ inches long.
Stigmas: Color—Sage Green 000861.
Ovaries: Superior.

My new variety of azalea is particularly distinguished by its brilliant red and white flowers each petal of which has a bright red base and main body part which color streaks lengthwise into a broad white border or margin. This new variety has the further advantage of early spring flowering and vigorous growth to produce a spreading pot-plant.

I claim:

1. A new and distinct variety of azalea plant substantially as herein shown and described, characterized by its vigorous and spreading growth and its profuse production of large flowers having petals with a broad white border surrounding a red colored base and body.

No references cited.

ROBERT E. BAGWILL, Primary Examiner